(12) United States Patent
Ma et al.

(10) Patent No.: US 10,059,719 B1
(45) Date of Patent: Aug. 28, 2018

(54) PROCESS FOR MAKING ISOIDIDE

(71) Applicant: Archer Daniels Midland Company, Decatur, IL (US)

(72) Inventors: Chi Cheng Ma, Forsyth, IL (US); Brennan Smith, Decatur, IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 15/756,624

(22) PCT Filed: Sep. 9, 2016

(86) PCT No.: PCT/US2016/050952
§ 371 (c)(1),
(2) Date: Mar. 1, 2018

(87) PCT Pub. No.: WO2017/044750
PCT Pub. Date: Mar. 16, 2017

Related U.S. Application Data (60) Provisional application No. 62/217,173, filed on Sep. 11, 2015.

(51) Int. Cl.
*C07D 493/04* (2006.01)
*B01J 21/18* (2006.01)
*B01J 23/755* (2006.01)
*B01J 23/46* (2006.01)

(52) U.S. Cl.
CPC ............ *C07D 493/04* (2013.01); *B01J 21/18* (2013.01); *B01J 23/462* (2013.01); *B01J 23/755* (2013.01)

(58) Field of Classification Search
CPC ....... C07D 493/04; B01J 21/18; B01J 23/462; B01J 23/755
See application file for complete search history.

(56) References Cited

U.S. PATENT DOCUMENTS

2014/0371472 A1* 12/2014 Hagberg .............. C07D 493/04
549/464

* cited by examiner

Primary Examiner — Timothy R Rozof
(74) Attorney, Agent, or Firm — William B. Miller (57) ABSTRACT

A process is provided for making isoidide, wherein a dextrose feed is first converted by a combination of epimerization and hydrogenation to an iditol-enriched mixture of hexitols in the presence of hydrogen and in the further presence of a single, dual purpose catalyst, and the iditol is then conventionally fully dehydrated to provide isoidide. In one general embodiment, the dehydration is performed on the iditol-enriched mixture of hexitols to provide an isohexides product mixture including isoidide, and the isoidide is recovered therefrom. In another general embodiment, iditol is separated from the iditol-enriched mixture of hexitols, and at least a portion of this iditol is then dehydrated to provide an isoidide product.

12 Claims, 2 Drawing Sheets

PROCESS FOR MAKING ISOIDIDE

The present application is a 371 National Phase Entry of International Patent Application PCT/US2016/050952 filed Sep. 9, 2016, which claims benefit of priority of U.S. Provisional Application No. 62/217,173, filed on Sep. 11, 2015, the contents of which are incorporated herein.

TECHNICAL FIELD

Background Art

The Value of Isoidide and Previous Methods for Making Via Iditol:

There are fundamentally three isohexides: isomannide, isoidide, and isosorbide. Isosorbide is a commercially-produced, bicyclic diol that is made by first hydrogenating dextrose to sorbitol, then double dehydrating the sorbitol to yield isosorbide. Its double hydroxyl function would make isosorbide of interest as a building block for polymerization. However, the making of polymers of suitable properties from isosorbide is hampered by the molecule's stereochemistry, with one endo hydroxyl group and one exo hydroxyl group, resulting in asymmetrical reactivity and amorphous polymers (due to the lack of symmetry). Its epimer isomannide, which has two endo hydroxyl groups, has proven to be unfavorable for polymerization due to low reactivity and low linearity. On the other hand, the epimer isoidide has two exo hydroxyl groups, and has been viewed as far better suited for use as a building block for polymerization than either isosorbide or isomannide. The symmetrical structure of isoidide eliminates the regiochemical reactivity difference between the two hydroxyl functionalities.

Examples of polymers wherein isoidide would be suitably used as a building block include polyesters made by polycondensation of isoidide and a dicarboxylic acid or anhydride, and polycarbonates made by reaction with a bifunctional carboxyl compound such as phosgene. Isoidide would also be suitably used in other polymerizations wherein conventionally other diols are used. For example, it has been considered that bisglycidyl ethers of isoidide could be used as a substitute for bisphenol-A in epoxy resins. Isoidide has also been used or proposed for use in place of petroleum-based monomers such as terephthalic acid, for instance.

Isoidide, however, is not currently manufactured on a commercial scale, in part (but not exclusively) because of the high cost of the synthetic precursor iditol from which isoidide might be made by an analogous double dehydration pathway as employed for making isosorbide.

U.S. Pat. No. 7,674,381 to Fuertes ("Fuertes") proposes one method of recovery of "highly pure" L-iditol, referencing the utility of L-iditol itself in food applications as a sweetener but also as a synthesis intermediate for the successive internal dehydration products iditan and isoidide (1,4,3,6-dianhydroiditol). Isoidide is described by Fuertes as useful as an osmotic or water-retaining agent, as a monomeric unit in polyesters, and as a further intermediate in the synthesis of diesters which could find use as plasticizers in synthetic resins or in the synthesis of diethers useful as solvents for certain pharmaceutical active agents or in certain polymers.

Fuertes contemplates various known pathways to L-iditol as a useful product in its own right as well as serving as a precursor for the desirable isoidide product for the applications mentioned by Fuertes and for the polymeric applications we've described above. The hydrogenation of L-idose is mentioned briefly as a possible method, but as Fuertes notes L-idose is not a naturally-occurring sugar that can be economically recovered from plants in the manner of other sugars such as dextrose. L-iditol itself may be found naturally in the fruit of the service tree (*Sorbus domestica* or *sorbus torminalis*) in small amounts, but again recovery on the commercial scale indicated by the potential applications of iditol and isoidide is deemed by Fuertes as self-evidently impracticable.

The hydrogenation of L-sorbose was known to produce a mixture of sorbitol and iditol, and at least one reference reviewed by Fuertes indicates that by selection of certain catalysts and/or the use of certain hydrogenation conditions, the proportions of the two enantiomers can be varied to an extent to produce additional iditol.

US 2004/0143024 to Yoshino et al. similarly describes that by the use of certain hydrogenation catalysts (Ru and Pt) D-iditol and L-sorbitol can be produced from D-sorbose in a ratio, respectively, of from about 70:30 to 50:50, while L-iditol and D-sorbitol can be produced from L-sorbose in respective proportion to one another of from 40:60 to 50:50 (again using Ru and Pt catalysts). Yoshino et al. further prescribe the use of an epimerase to generate the less common sugars from the more common sugars such as dextrose and fructose, in order for the less common sugars to be hydrogenated selectively in this manner.

The isomerization of readily available hexitols such as sorbitol had also been known as a way to make the iditol precursor. An article by Wright and Hartman from 1961 is summarized as describing the production of an equilibrium mixture of 50% of sorbitol, 25% of mannitol and 25% of iditol through epimerization at 170 degrees Celsius, under a hydrogen pressure of 1900 psi and in the presence of a nickel catalyst.

Both of these pathways are said to prove iditol in "noticeable amounts", however, they are also dismissed as commercially impractical because of poor purity and poor yield considerations due to the appearance or the persistence in the reaction medium of other polyols which are indicated as separated from the desired iditol product only with considerable difficulty.

Fuertes additionally references two published biological methods for reduction of L-sorbose virtually exclusively to L-iditol, but indicates that neither method provided iditol with a yield and a purity "sufficiently high for industrial companies to be able to have this hexitol available to them in an abundant amount and under advantageous cost conditions" col. 2, lines 39-41; one method in this regard was said to provide 50 grams/liter of iditol from 150 g/l of L-sorbose in five days (with no remaining L-sorbose), but direct crystallization of the iditol from the fermentation medium was termed "impossible", while the second method reviewed was described as "extremely complex and delicate" and as providing no teaching regarding recovery of the iditol from the fermentation medium.

Fuertes' method of producing "highly pure" iditol relies on the production of iditol from L-sorbose according to a known method involving hydrogenation of L-sorbose followed by bacterial oxidation of the L-sorbose/iditol mixture obtained by means of the hydrogenation, but introduces a chromatographic fractionation on cationic resins or zeolites, with such cationic resins as have been used previously for the separation of sugars such as fructose and glucose or for the separation of polyols such as sorbitol and mannitol being preferred.

Other Methods for Making Isoidide, Via Epimerization of Isosorbide:

An alternative pathway to isoidide through the epimerization of isosorbide has been investigated as a way of getting around the lack of a commercial supply of iditol from which isoidide might be made, though the literature related to this alternative pathway is quite limited. In one recent publication, LeNotre et al. reported a highly efficient method for obtaining resin-grade isoidide through catalytic epimerization of isosorbide using a ruthenium-on-carbon catalyst (LeNotre et al. "Synthesis of Isoidide through Epimerization of Isosorbide using Ruthenium on Carbon" ChemSusChem 6, 693-700, 2013). This reference shows the synthesis of isoidide from highly purified (>99.5% pure) isosorbide (Polysorb, Roquette, Lestrem, France).

WO 2013125950A1, filed Feb. 20, 2012 for "Method of Making Isoidide" and published Aug. 29, 2013 (the "WO'950 application" or "WO'950") is related and describes a process for the preparation of isoidide from isosorbide, wherein an aqueous solution of isosorbide is subjected to epimerization in the presence of hydrogen under the influence of a catalyst comprising ruthenium on a support, at a starting pH of above 7. WO'950 further provides a process for the preparation of isoidide from glucose by hydrogenating glucose to form sorbitol, fully dehydrating the resulting sorbitol to form isosorbide, then epimerizing the isosorbide into isoidide using a catalyst comprising carbon-supported ruthenium.

One perceived challenge to the practical commercial fulfillment of this alternative pathway has been the difficulty, in light of the very high purities demanded by polymer manufacturers for monomer feedstocks, of producing a highly pure isosorbide feed for being epimerized to in turn produce the needed very high purity isoidide. Conventionally speaking, to produce very high purity products it is thought necessary (or at least highly desirable) to use high purity starting materials, and the conversion of sorbitol to isosorbide by an acid-catalyzed double dehydration has long been recognized as plagued by vexing side reactions in which unwanted by-products are formed; consequently, a substantial amount of work has been undertaken (albeit largely for the purpose of producing and selling a monomer grade isosorbide rather than a monomer grade isoidide product) to develop methods whereby the side reactions are diminished.

A number of prior filed applications demonstrate the extent of efforts to develop such methods, including, for example, the above-mentioned WO'950 application; WO 2013138153 (using certain substituted sulfonic acid catalysts for the dehydration); WO 2014070371 (addressing stabilizing isosorbide against degradation on storage); WO 2014070369 (using ion exchange, ion exclusion or both ion exchange and ion exclusion with hydrogenation to provide improved color isosorbide); WO 2014070370 (using antioxidants with the crude dehydration product mixture that distill with isosorbide); WO 2014137619 (using certain water-tolerant metal triflate, Lewis acid catalysts for the dehydration); WO 2015112389 (performing the dehydration using a thin film evaporator); WO 2015156839 for "Phosphonic Acid Catalyst in Dehydrative Cyclization of Five and Six Carbon Polyols with Improved Color and Product Accountability"; and WO 2015156846 for "Dehydration of a Sugar Alcohol with Mixed Combination of Acid Catalysts".

In particular, sorbitans are the primary byproducts in the isosorbide synthesis from sorbitol, and have been recognized as causing significant problems with color development and isosorbide degradation over time. Previously mentioned International Application No. WO 2014070371 A1 thus relates at least in part to the removal of sorbitans from sorbitol by distillation. Further, previously mentioned International Application No. WO 2014070369 A1 cites prior Japanese patent application JP 2006/316025 as assigning responsibility for color development and degradation problems to the auto oxidation of sorbitans in isosorbide and to unspecified "side reactions" involving a solvent (such as water and organic solvents such as xylene and toluene) from the dehydration of sorbitol to make isosorbide. The JP'025 reference prescribes multiple distillations of the crude isosorbide in the absence of a solvent at gradually increasing temperatures and/or at least one such solventless distillation followed by thermal treatment of the isosorbide to reduce the 1,4-sorbitan content of the isosorbide product, with bleaching of the isosorbide product included in each case by treating with ion exchange resins and carbon adsorption.

A further perceived challenge to the realization of a commercial process for producing isoidide via epimerization from isosorbide has come from the fact that even when highly pure isosorbide is obtained and used in an epimerization process as originally described by Le Notre et al. in their journal article, a set of byproducts are nevertheless formed that with the isomannide and isosorbide epimers pose still further difficulties for obtaining the ultimately desired monomer grade purity isoidide product. The WO'950 application thus teaches in reference to Le Notre et al.'s proposed process that a method for making isoidide while avoiding side reactions is desirable, referencing yield-reducing side reactions that lead to undesirable mass loss, e.g. as a result of hydrodeoxygenation. The products of these side reactions included non-volatile hydrodeoxygenation (HDO) products (diols).

Yet another challenge to an epimerization-based method for making isoidide from isosorbide relates to the separation of the isomeric products isosorbide, isoidide and isomannide from the crude epimerization product mixture. The separation of these isomers has generally been by fractional distillation; while distillation is effective to a certain extent, the isohexides have relatively close boiling points at elevated temperatures and reduced pressures, resulting in added cost and complexity for carrying out the separation by distillation alone.

A number of these challenges have been addressed by two commonly-assigned applications, WO 2016137833 published Sep. 1, 2016 for "Isoidide Manufacture and Purification" and WO 2016137835 also published Sep. 1, 2016 under the same title.

In the former, it was found that when isoidide is made by epimerization of an isosorbide composition in which certain isosorbide reaction by-products have been allowed to remain or even introduced—from an impure isosorbide containing these certain isosorbide reaction by-products (hereafter, "impure isosorbide")—hydrodeoxygenation by-products were formed that were volatile and easily separated from the isoidide product during evaporative water removal. Further, reduced losses to side products are seen in the subsequent epimerization, when the epimerization is performed on these less-pure isosorbide feeds as compared to more highly purified isosorbide feeds. As a consequence, purification requirements are reduced in relation to the isosorbide feed, isoidide yields are improved and purification of the isoidide is facilitated.

In the latter, related application, the impurities in an isoidide obtained from a less pure isosorbide feed after epimerization are found to be such that the purification to a polymer grade isoidide is made possible by means other by than the previously prescribed fractional distillation—namely, by one or more of ultrafiltration, nanofiltration, ion exclusion chromatography, ion exchange chromatography, simulated moving bed chromatography, and contacting with activated carbon, followed in certain embodiments by crystallization. Crystals of essentially pure isoidide were achieved, and by carrying out the purification without subjecting the epimerization product to distillation temperatures, substantial cost savings can be realized and the heat-sensitive isohexides included in the epimerization product can be spared the damaging effects of high temperatures.

Nevertheless, even with the significant advances that have been made in relation to the manufacture of isoidide via an epimerization of isosorbide, it would be desirable to be able to produce isoidide without on the one hand also being required to produce isosorbide, provided this could be accomplished more simply and directly than by the complex, multistep approaches described in Fuertes. Even in the circumstance where isosorbide may be considered a valuable co-product to be made, it would be desirable to also be able to produce isoidide other than through epimerization from isosorbide with its attendant hydrodeoxygenation yield losses.

SUMMARY OF THE INVENTION

The following presents a simplified summary of the invention in order to provide a basic understanding of some of its aspects. This summary is not an extensive overview of the invention and is intended neither to identify key or critical elements of the invention nor to delineate its scope. The sole purpose of this summary is to present some concepts of the invention in a simplified form as a prelude to the more detailed description that is presented later.

With this understanding, the present invention in one aspect relates to a chemocatalytic process for making isoidide, wherein a dextrose feed is first converted by a combination of epimerization and hydrogenation to an iditol-enriched mixture of hexitols in the presence of hydrogen and in the further presence of a single, dual purpose catalyst, and the iditol (normally in the form of a mixture of the L- and D-iditol isomers; "iditol" as used henceforth in reference to the inventive process will accordingly be understood as embracing both L- and D-iditol isomers) is then conventionally fully dehydrated to provide isoidide.

In one general embodiment, the dehydration is performed on the iditol-enriched mixture of hexitols to provide an isohexides product mixture including isoidide, and the isoidide is recovered therefrom.

In another general embodiment, iditol is separated from the iditol-enriched mixture of hexitols, and at least a portion of this iditol is then dehydrated to provide an isoidide product.

DESCRIPTION OF EMBODIMENTS

As used in this application, the singular forms "a", "an" and "the" include plural references unless the context clearly indicates otherwise. The term "comprising" and its derivatives, as used herein, are similarly intended to be open ended terms that specify the presence of the stated features, elements, components, groups, integers, and/or steps, but do not exclude the presence of other unstated features, elements, components, groups, integers and/or steps. This understanding also applies to words having similar meanings, such as the terms "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers, and/or steps. The term "consisting essentially of", as used herein, is intended to specify the presence of the stated features, elements, components, groups, integers, and/or steps, as well as those that do not materially affect the basic and novel characteristic(s) of stated features, elements, components, groups, integers, and/or steps. Terms of degree such as "substantially", "about" and "approximately" as used herein mean a reasonable amount of deviation of the modified term (beyond that degree of deviation understood by the precision (significant figures) with which a quantity is expressed) such that the end result is not significantly changed. These terms of degree should be construed as including a deviation of at least plus or minus five (5) percent from the stated value, provided this deviation would not negate the meaning of the term modified.

Unless otherwise indicated, any definitions or embodiments described in this or in other sections are intended to be applicable to all embodiments and aspects of the subjects herein described for which they would be suitable according to the understanding of a person of ordinary skill in the art.

Figure 1:
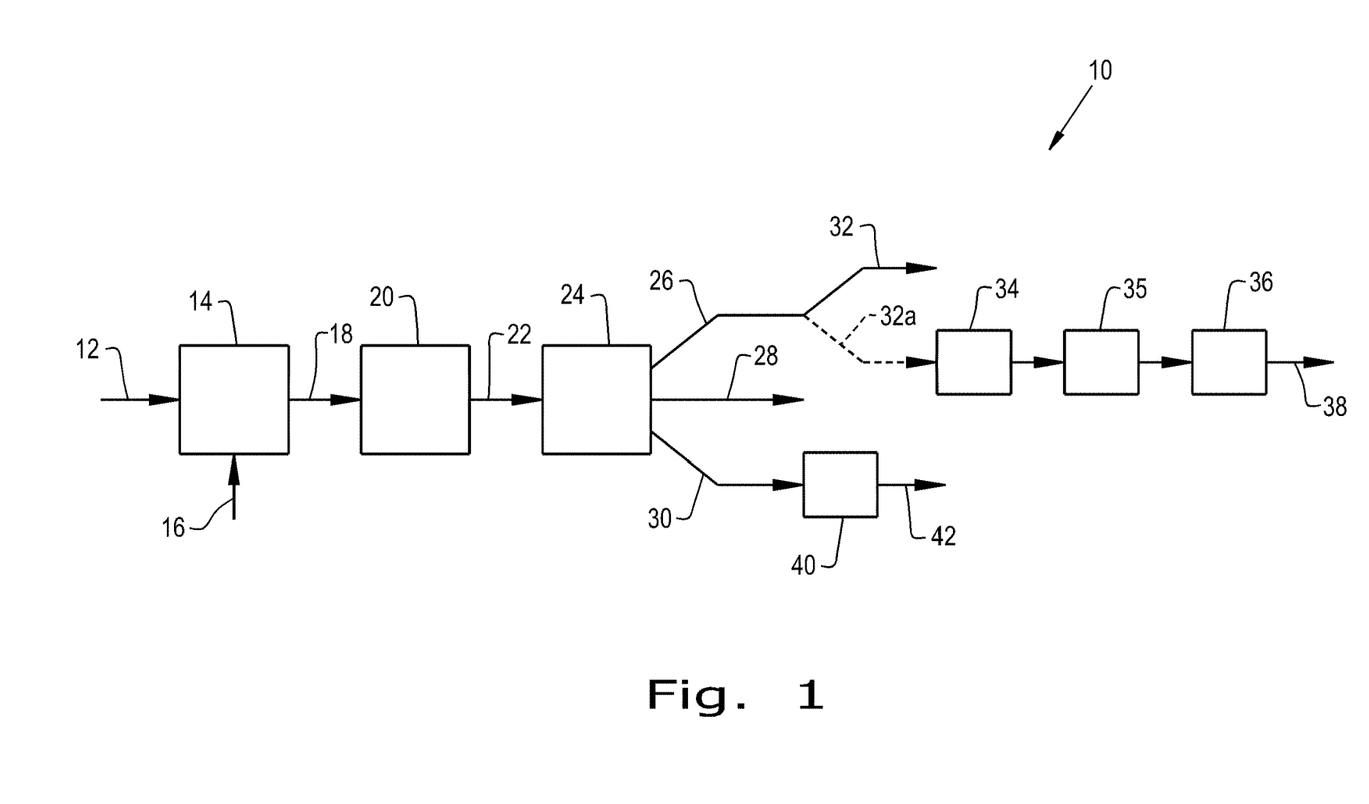
FIG. 1 is a schematic depiction of a process of the present invention according to the first general embodiment summarized above (and including several optional further steps related to producing an isosorbide co-product and/or additional isoidide through epimerization from at least a portion of the isosorbide co-product), wherein an iditol-enriched mixture of hexitols is produced and then dehydrated to provide a mixture of isohexides including isoidide, and a separation is undertaken or series of separations are undertaken on the mixture of isohexides, with further purification of at least the isoidide recovered from the mixture of isohexides.

Turning now to FIG. 1, a process of the present invention is schematically illustrated in a first, general embodiment 10, wherein a feed comprising dextrose 12 is supplied to a reactor 14 wherein the dextrose is converted in the presence of hydrogen 16 and in the further presence of a combined epimerization/hydrogenation catalyst to a product comprising a mixture of hexitols (18) that is enriched in iditol, having an iditol content above that attributable strictly to the hydrogenation of hexoses and also above that attributable strictly to the epimerization of hexitols. An "iditol-enriched mixture of hexitols" will typically be characterized by a selectivity to and yield of iditol of at least 5 percent by weight from dextrose, preferably at least 15 percent, more preferably at least 30 percent, and most preferably at least 40 percent. From another perspective, an iditol-enriched mixture of hexitols will typically be characterized by an iditol:

other hexitols mass ratio of at least 1:10, preferably at least 1:5, more preferably at least 1:3, and most preferably at least 1:2.

As shown in the examples provided herein, suitable combined epimerization/hydrogenation catalysts include sulfided ruthenium on carbon and sponge nickel catalysts such as produced by Johnson Matthey, London, United Kingdom. Useful hydrogen pressures range from 8.3 MPa, gauge (1200 psi, gauge) to 17.2 MPa, gauge (2500 psig) at temperatures between 100 to 200 degrees Celsius, but preferably hydrogen will be supplied to the combined epimerization/hydrogenation step at a pressure from 11.0 MPa, gauge (1600 psig) to 13.8 MPa, gauge (2000 psig) and the reaction temperature will be from 130 to 180 degrees Celsius. The best results to date were seen with a sponge nickel catalyst from Johnson Matthey at a reaction temperature of 170 degrees Celsius, using 12.4 MPa, gauge (1800 psig) hydrogen and a liquid hourly space velocity of 1.

The iditol-enriched mixture of hexitols 18 is then fully dehydrated in a step 20 to provide a product comprising a mixture of isohexides 22. Methods for accomplishing the dehydration step 20 are well-known, and may include, for example, any of the known methods for producing isosorbide from sorbitol.

One such method may be as described in WO 2015112389, wherein sorbitol or another hexitol or a combination of hexitols is described as continuously dehydrated in the presence of an acid catalyst under vacuum using a thin film evaporator, where "thin film evaporator" comprehensively embraced thin film evaporators, wiped film evaporators, short path evaporators, falling and climbing film evaporators, falling and climbing film plate evaporators and any similar device wherein a fluid moves across or over a heated surface as opposed to being heated in a continuous bulk mass wherein heat is transferred in the main from one portion of the fluid to another. Conducting the dehydration in the prescribed manner was said to enable a continuous process to be conducted at comparatively lower temperatures and with a reduced thermal history for the mono- and dianhydrohexitols produced from the dehydration, given the well-appreciated thermal sensitivity of these materials. Other methods or approaches can be used, including, for example, a continuous flow stirred tank reactor (CSTR), and batch, semibatch and continuous modes of operation can be contemplated.

Conventionally processes for the dehydration of sorbitol and the like are acid-catalyzed. A variety of acid catalysts have been described in the literature as suited for accomplishing the dehydration of hexitols to the corresponding isohexides, including, but not being limited to the catalysts described in the following commonly assigned patent and applications for patent: the certain poorly soluble substituted sulfonic acid catalysts described in U.S. Pat. No. 9,090,759 to Binder et al., "Process For Making Sugar And/Or Sugar Alcohol Dehydration Products"; the water-tolerant metal triflate catalysts described in WO 2014/137619 to Stensrud et al.; phosphonic acid as described in WO 2015156839; and a mixed-acid catalyst reaction mixture containing a reducing Brønsted acid, having a pKa of about 1.0-1.5, in combination with at least a strong Brønsted acid or a Lewis acid, having a pKa<0, or both kinds of strong Brønsted and Lewis acids in a solution, as described in WO 2015156846. Preferably, a strong Brønsted acid catalyst with an acid dissociation constant Ka such that the negative base 10 logarithm of its acid dissociation constant (conventionally expressed as pKa) is less than about −1.5 is used, such acids providing (by our testing) the greatest conversion, yield and accountability for the dehydration of sorbitol to isosorbide in the shortest timeframe. An example of a strong Brønsted acid catalyst with a pKa of less than −1.5 is sulfuric acid, for example, in the form of an aqueous solution of from 0.3 to 3.0 mol percent, preferably from 0.75 to 2.0 and still more preferably from 1.0 to 1.5 mol percent of sulfuric acid, which would be employed at a temperature in the range of from 110 to 200 degrees Celsius, preferably from 125 deg. C. to 175 deg. C., and still more preferably from 130 to 150 degrees Celsius for from 10 minutes to 180 minutes, preferably from 30 minutes to 120 minutes, and more preferably from 60 minutes to 90 minutes.

Following the dehydration step 20, a mixture of isohexides 22 is then further processed for being separated in step 24 into at least a first fraction 26 principally and preferably comprised substantially entirely of all of the isosorbide from the isohexides in mixture 22, a second fraction 28 principally and preferably comprised substantially entirely of all of the isomannide from the isohexides in mixture 22, and a third fraction 30 principally and preferably comprised substantially entirely of all of the isoidide from the isohexides in mixture 22. Depending on the efficiency with which isosorbide, isomannide and isoidide are fractionated in step 24, preferably the isosorbide, isomannide and isoidide fractions 26, 28 and 30, respectively, contain less than 1000 parts per million by weight, more preferably less than 500 ppm, and still more preferably less than 100 ppm by weight of other isohexides than the isohexide desired to be collected in a given fraction.

The further processing in step 24 in one embodiment includes the application of a number of techniques as described in detail in "Improved Method of Making Internal Dehydration Products of Sugar Alcohols", WO 2014070371, in order to ultimately produce fractions 26, 28 and 30 which are suited for certain immediate uses and for any further purification as may be indicated to achieve polymer-grade purities.

Initially, after neutralization to guard against such degradative losses as might otherwise be experienced through overexposure to strongly acidic conditions, nanofiltration or ultrafiltration may be carried out on the mixture 22 according to this embodiment to reduce higher molecular weight, oligomeric or polymeric impurities in the product mixture 22 that may precipitate out and foul subsequent ion exchange and/or ion exclusion resins. Membranes having a molecular weight cut-off of from 1,000 to 10,000 should be useful for this purpose. Examples of the membranes we have tried and found useful under our particular conditions include GE Power™ and Water GE™-series, and PW™-series polyethersulfone ultrafiltration membranes, Sepro™ PES5, PES10 polyethersulfone, and PVDF4™ polyvinylidine fluoride ultrafiltration membranes.

In an embodiment, following the nanofiltration or ultrafiltration step, an ion exclusion step is employed for removing ionic species from the filtered mixture through simulated moving bed chromatography using at least one strong acid cation exchange resin. Preferred resins are chromatographic grade, gel type resins with a volume median diameter between 290-317 µm, where more than 80% of the particle size range is between 280-343 µm and more than 60% of the particle size range is between 294-392 µm, which are characterized by a crosslink density of less than 12%, more preferably less than 8% and ideally less than 6%, and which are in the cation form corresponding to the highest concentration cation present in the filtered isohexide mixture. The ion exclusion step may be conducted in a batchwise, semibatch or continuous manner and may be conducted through a fixed bed arrangement or a continuous simulated moving bed system.

In a particular embodiment, the ion exclusion step is followed by an ion exchange step for removing additional ionic impurities, through the use of preferably a fixed bed arrangement including at least one highly crosslinked strong acid cation exchange resin in the hydrogen form and one macroporous, highly crosslinked strong base anion exchange resin in the hydroxide form. As with the materials used for the ion exclusion step, while particular examples follow hereafter, various resins of the indicated types are commercially available and known to those skilled in the art, and it will be well within the capabilities of those of ordinary skill in the use of such ion exchange resins to select and use appropriate resins effectively in the ion exchange step to remove additional impurities of the types listed above from the mixture 22.

A carbon or resin bed adsorption step may be used in an embodiment, principally to remove further nonionic oligomeric and polymeric impurities and/or color bodies that may remain. Preferably a fixed bed arrangement with one or more activated carbons is used. Suitable activated carbons include but are not limited to Norit™ SA2 steam activated carbon from peat, Calgon CPG™-LF low acid soluble iron content granular activated carbon from coal, Calgon CAL™ coal-based granular activated carbon, Nuchar™ SN chemically activated, wood-based powdered activated carbon, Norit™ RO 0.8 high surface area pelletized activated carbon, Nuchar™ WV-B low density, high surface area granular activated carbon, Calgon PCB™ activated carbon from coconut shells, Calgon BL™ powdered, reagglomerated coal-based activated carbon, Nuchar™ RGC high activity, low ash, low soluble iron granular activated carbon, and Nuchar™ SA-20 chemically activated, wood-based powdered activated carbon. Suitable adsorptive resins include but are not limited to macroporous styrene-divinylbenzene type resins, for example, Dowex Optipore™ L493 and Dowex Optipore SD-2™ resins.

At any point before, during, or after being subjected to one or more of ultrafiltration, nanofiltration, ion exclusion chromatography, ion exchange chromatography, simulated moving bed chromatography, and/or contacting with activated carbon, the water content of the mixture 22 may be adjusted, such as by evaporation or adding water.

As described in WO 2014070371, the mixture 22 may then be resolved into the fractions 26, 28 and 30 by one or more of distillation, solvent recrystallization, melt crystallization, and solvent washing and filtration. Preferably simple distillation is used, in particular through use of a thin film evaporator. As well, one or more antioxidants are added to the mixture 22 prior to its distillation as described in WO 2014070370.

The separation of fractions 26, 28 and 30 in step 24 may be accomplished in an alternate embodiment by simulated moving bed chromatography, for example, as demonstrated in the examples of WO 2016137835, using a strong acid cation exchange resin in the $Ca^{2+}$ cation form, or by packed column distillation or other alternative, known methods as briefly summarized in WO 2016137835 in relation to prior art approaches.

The first isosorbide fraction 26 processed in this manner will preferably be at least of a quality to be used directly (as indicated by stream or flow 32) in certain applications as is, or in other embodiments may be further processed or purified as appropriate to provide a more highly pure and/or more color stable material as may be desired for manufacturing certain polymers. Thus, for example, hydrogenation, distillation and/or antioxidant additives may be employed as described in "Hydrogenation of Isohexide Products for Improved Color", WO 2014070369, and/or as described in "Additives for Improved Isohexide Products", WO 2014070370. Other methods of purifying a crude isosorbide are known and may be employed in other embodiments, for example, the combination of chromatography and crystallization techniques described in WO 200239957 to Dalziel et al.

In another embodiment, at least a portion 32a of the first isosorbide fraction 26 may be diverted for producing additional isoidide therefrom by epimerization in an epimerization step 34. In one embodiment, a process may be used of a type described in WO 2013125,950, filed Feb. 20, 2012 for "Method of Making Isoidide", wherein an aqueous solution of isosorbide is subjected to epimerization in the presence of hydrogen under the influence of a catalyst comprising ruthenium on a support, especially, a carbon support, at a starting pH of above 7.

In another embodiment, an epimerization process as taught by Wright and Brandner, J. Org. Chem., 1964, 29 (10), pp 2979-2982 can be used, employing Ni catalysis, especially using nickel supported on diatomaceous earth, under relatively severe conditions, such as a temperature of 220° C. to 240° C. at a pressure of 150 atmosphere. A similar disclosure is to be found in U.S. Pat. No. 3,023,223.

In still another embodiment, an epimerization process as described in WO 2016137833 may be used dependent upon the purity of the first isosorbide fraction 26. In this regard, it was found that by epimerizing an impure isosorbide composition containing measurable sorbitans, reduced hydrodeoxygenation yield losses are made possible as compared to a more highly purified isosorbide fraction 26 containing little to none (meaning effectively a non-detectable quantity) of the sorbitans. Consequently, where it is anticipated that a substantial proportion of the isosorbide fraction 26 may be applied in a portion 32a for making isoidide, it may be possible to realize some savings in the separation step 24. Hydrodeoxygenation yield losses, expressed in terms of weight percent (wt. %) of the starting isosorbide in fraction 26, may be no greater than 22 wt. %, no greater than 21 wt. %, no greater than 20 wt. %, no greater than 19 wt. %, no greater than 18 wt. %, no greater than 17 wt. %, no greater than 16 wt. %, no greater than 15 wt. %, no greater than 14 wt. %, no greater than 13 wt. %, no greater than 12 wt. %, no greater than 11 wt. %, no greater than 10 wt. %, no greater than 9 wt. %, no greater than 8 wt. %, no greater than 7 wt. %, no greater than 6 wt. %, no greater than 5 wt. %, no greater than 4 wt. %, no greater than 3 wt. %, no greater than 2 wt. %, no greater than 1 wt. %, no greater than 0.5 wt. %, no greater than 0.1%.

Without wishing to be bound by theory, it is believed that the sorbitans decompose in the epimerization reactor to form compounds having boiling points below the boiling point of the desired isoidide. These include hydrodeoxygenation (HDO) products; HDO products have been characterized as a mixture of straight chain aliphatic alcohols with low boiling points relative to isohexides (volatiles: propanols, butanols, hexanols, alkanes; nonvolatiles: propanediols, butanediols, hexanediols, furanol; (supporting information for LeNotre et al., ChemSusChem 6, 693-700 2013 at http://onlinelibrary.wiley.com/store/10.1002/cssc. 201200714/asset/supinfo/cssc_20120071 4_sm_miscellaneous_information.pdf?v=1&s=89d9ec835660174ab84c-20ed 377959f2d1e0a55c, accessed Nov. 19, 2014)).

The impure isosorbide feedstocks contemplated in WO 2016137833 are characterized by a ratio of isohexide content to sorbitan content (in weight percent) ranging from one to two hundred, including the endpoints and the entire range, i.e., ranging from 50% isohexide/50% sorbitans to 99.5% isohexides/0.5% sorbitans where the content in weight percent of isohexides and sorbitans in the composition is normalized to 100%.

Further, the HDO compounds generated in the epimerization of an impure isosorbide fraction 26 were found to have boiling points below the boiling point of the desired isoidide, and accordingly were readily removed by simple evaporation. In a particular embodiment, the remaining isoidide may be purified to a polymer-grade purity isoidide product 38 in a manner illustrated and exemplified in WO 2016137833, wherein a combination of simulated moving bed chromatography using a strongly acidic cation exchange resin in the $Ca^{2+}$ cation form (indicated by step 35 in the schematic process of FIG. 1) and single stage, selective recrystallization with water and a single, finishing water wash of the crystals recovered (the recrystallization and final water wash being indicated by step 36 of FIG. 1) therefrom gave crystals containing 100% isoidide (Ex. 10).

The third, isoidide fraction 30 from separation step 24 may be similarly purified in a purification step 40 by a combination of simulated moving bed chromatography using a strongly acidic cation exchange resin in the $Ca^{2+}$ cation form and single stage, selective recrystallization with water and a single, finishing water wash to yield a polymer grade isoidide product 42 that is at least 99.5 percent pure in isoidide, preferably being at least 99.7 percent pure, more preferably at least 99.8 percent pure and most preferably being at least 99.9 percent pure in isoidide.

Figure 2:
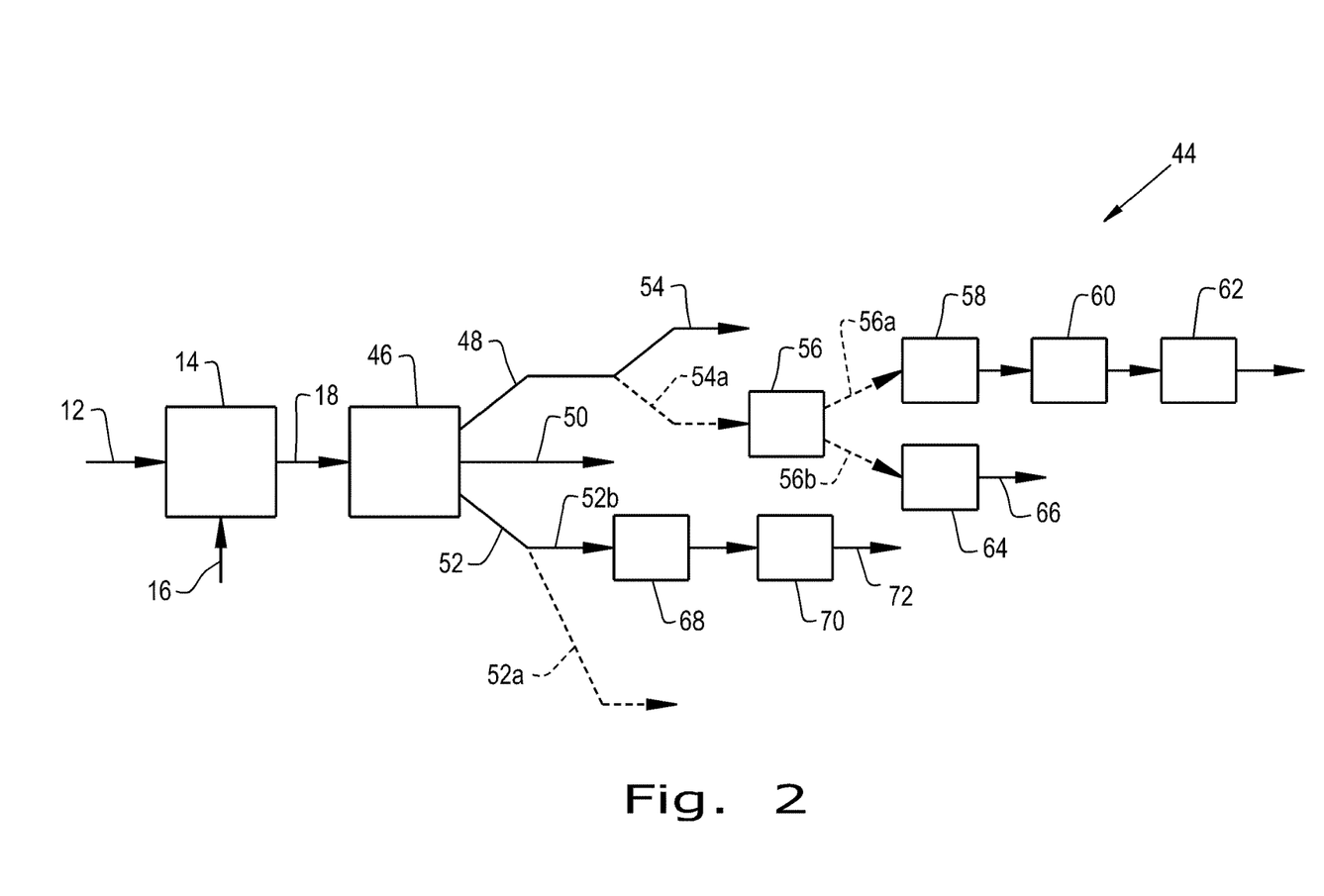
FIG. 2 is a schematic depiction of a process of the present invention according to an alternative, general embodiment, wherein an iditol-enriched mixture of hexitols is produced and a separation is undertaken or series of separations are undertaken to separate iditol from the mixture of hexitols for its subsequent dehydration to provide isoidide. As in FIG. 1, options for various co-products are also included in the schematic and will be described hereafter.

Turning now to FIG. 2, an alternative, general embodiment of the present invention is illustrated schematically, wherein an iditol-enriched mixture of hexitols is produced and a separation is undertaken or series of separations are undertaken to separate iditol from the mixture of hexitols prior to its dehydration to produce an isoidide product. More particularly, an illustrative embodiment 44 is provided, wherein as in the embodiment of FIG. 1 a feed comprising dextrose 12 is first supplied to a reactor 14 wherein the dextrose is converted in the presence of hydrogen 16 and in the further presence of a combined epimerization/hydrogenation catalyst to a product comprising a mixture of hexitols (18) that is enriched in iditol, having an iditol content above that attributable strictly to the hydrogenation of hexoses and also above that attributable strictly to the epimerization of hexitols.

Rather than dehydrating the mixture 18 as in FIG. 1 and then seeking to recover and purify the isoidide from the resultant mixture of isohexides, however, in the illustrative embodiment 44 of FIG. 2 a separation step 46 is performed on the hexitols mixture 18 to provide a first fraction 48 principally and preferably comprised substantially entirely of all of the sorbitol from the hexitols in mixture 18, a second fraction 50 principally and preferably comprised substantially entirely of all of the mannitol from the hexitols in mixture 18, and a third fraction 30 principally and preferably comprised substantially entirely of all of the iditol from the hexitols in mixture 18. Depending on the efficiency with which sorbitol, mannitol and iditol are fractionated in step 46, preferably the sorbitol, mannitol and iditol fractions 48, 50 and 52, respectively, contain less than 5.0 percent by weight, more preferably less than 2.0 percent and still more preferably less than 0.5 percent by weight of other hexitols than the hexitol desired to be collected in a given fraction.

In one embodiment, the separation in step 46 of sorbitol, of mannitol and of iditol from one another from within the mixture 18 will be accomplished chromatographically. In this regard, Angyal, "Chromatography on Cation Columns: a Much-Neglected Method of Separation", *Aust. J. Chem.* 2002, vol. 55, pp. 79-81 (2002) reports that a cation exchange column in the $Ca^{2+}$ form used extensively in the food industry to produce fructose-enriched syrups is also effective for separating all of the hexitols from one another, and particularly suggests the use of such columns for recovering the more rare, minor products from an epimerization. While a column in the $Ca^{2+}$ form is thus indicated as capable of performing the separation, after noting a prior 1989 study finding that the middle lanthanide cations, and particularly Eu, Sm and Nd, form much stronger complexes with polyols than does Ca, with Nd being preferred as the least expensive of these three, Angyal provides an example of the separation of D-mannitol, D-glucitol (sorbitol) and D-iditol using a strong acid cation exchange resin in the $Nd^{2+}$ form. More particularly, 0.5 gram samples of each of these were supplied to a 14.0 by 2.2 cm column of Dowex® 50W-X4 strong acid cation resin in the $Nd^{2+}$ form, with water being supplied at 50 mL/hr as the eluent and with collecting 10 mL fractions. Mannitol was the first to emerge, in 60 to 90 mL of eluent, followed by glucitol/sorbitol in 100-130 mL and then iditol in 120-210 mL of eluent. Since there was some overlap between the glucitol/sorbitol and iditol, a slightly longer column was observed as needed to give complete separation.

Similarly, Petrus et al., "Chromatographic Separation of Alditols on a Cation-Exchange Resin in the Lanthanum Form", *Chem. Zvesti*, vol. 34, no. 4, pp. 530-536 (1980) report successfully separating D-mannitol, D-glucitol and L-iditol among a number of other alditols in a mixture, using water as an eluent, with a strong acid cation exchange resin in the lanthanum form (Dowex® 50W X8, 200/400 mesh). Results are also provided for a $Ca^{2+}$ form resin to indicate that a column of this material would be suitable for accomplishing the separation, though it was reported that the lanthanum form would be more effective.

In other embodiments, the separation in step 46 may be accomplished through crystallization methods or by a combination of chromatography and crystallization techniques. In this regard, there are a number of well-known and industrially practiced methods for the separation of mannitol and sorbitol that could be adapted for application to a mixture of sorbitol and mannitol with iditol; such methods are well-known, as described, for example, in DE 10063973A1 to Konetzke e al (2002) and U.S. Pat. No. 3,864,406 to Melaja et al. (1975), the latter describing a capability for obtaining pure mannitol and pure sorbitol from an aqueous solution of a mixture of these through a single crystallization step. Preferably, however, the separation in step 46 will be carried out using chromatography, especially simulated moving bed chromatography.

The first sorbitol fraction 48 may be employed directly in established applications and end uses for sorbitol as produced, for example, by the hydrogenation of dextrose, as suggested by stream 54. Alternatively, in an embodiment at least a portion 54a may be dehydrated in a step 56 to provide isosorbide, which may in turn be used in certain embodiments schematically suggested in FIG. 2, namely, for making isoidide in a manner as described above, for being purified as appropriate for polymeric and other high-purity applications or for use both for making isoidide and for the just-mentioned polymeric and other high purity applications.

Thus, at least a portion 56a of isosorbide from a dehydration 56 performed on the fraction 48 may undergo epimerization in a step 58, with purification by simulated moving bed chromatography in a step 60 and by crystallization in a step 62 all as substantially described above in reference to steps 34, 35 and 36 of FIG. 1, to provide a purified isoidide product 62 preferably suitable for polymeric applications, having a purity of least 99.5 percent, more preferably at least 99.7 percent, still more preferably at least 99.8 percent and most preferably at least 99.9 percent.

In another option, at least a portion 56b of the isosorbide from the dehydration step 56 may be processed in the manner described above in paragraphs 0037-0043 in relation to step 24 in FIG. 1, and optionally further processed or purified as appropriate for certain uses, as described in paragraph 0044. The processing of portion 56b according to paragraphs 0037-0043, and the optional further processing according to paragraph 0044, are both understood as represented in FIG. 2 by a step 64 and provide commercially suitable, finished isosorbide in stream 66. Other methods of purifying a crude isosorbide are known and may be employed in other embodiments to further purify portion 56b, for example, the combination of chromatography and crystallization techniques described in WO 2002/39957 to Dalziel et al. mentioned above.

Turning now to the iditol fraction 52, in an embodiment at least a portion 52a of the iditol may be used as a sweetener or as a synthesis intermediate in the preparation of other products, as suggested in U.S. Pat. No. 7,674,381 to Fuertes e al. The remainder 52b may be conventionally dehydrated in step 68 by analogous methods to those found useful for forming isosorbide from sorbitol, and then the isoidide may be purified in a step 70 as necessary for a given application or end use to provide a commercially suitable, finished isoidide 72. Methods of purifying isoidide have been described in the above-referenced WO 2016137833, wherein a combination of simulated moving bed chromatography using a strongly acidic cation exchange resin in the Ca$^{2+}$ cation form and single stage, selective recrystallization with water and a single, finishing water wash of the crystals recovered, though other methods again analogous to those developed for the purification of isosorbide can be employed for both step 70 in FIG. 2 and step 40 in FIG. 1. Examples of such alternative processes may be found in WO 2014199399 to Uppara et al. and the various background references cited therein, wherein for the process claimed by Uppara et al. colored impurities are eliminated by dispersing the product from the dehydration step (68 in our process) in a suitable diol and then adsorbing these by means of adsorption aids.

The present invention is further illustrated by means of the following, non-limiting examples:

EXAMPLE 1

A ruthenium on carbon catalyst including 2 percent of ruthenium based on the total weight of the catalyst was loaded into a 30 cubic centimeter fixed bed reactor, and hydrogen was thereafter supplied to the reactor at 11.0 MPa, gauge (1600 pounds per square inch, gauge), at a rate of 0.4 liters per minute, together with a liquid feed comprised of 20% dextrose and the remainder of water. The reactor temperature was 130 degrees Celsius, and the liquid hourly space velocity was 1 hr$^{-1}$.

The process was continuously run over a period of two weeks, with product samples being drawn on a number of consecutive days within that timeframe. All amounts are reported as percent by total weight.

TABLE 1

| Products | MANNITOL/ ARABITOL % | DULCITOL/ XYLITOL % | SORBITOL % | IDITOL % |
| --- | --- | --- | --- | --- |
| Ru/C | 5.986 | 1.382 | 15.785 | 4.91 |

COMPARATIVE EXAMPLES 2-4

A commercially available Raney nickel catalyst was loaded into a 30 cubic centimeter fixed bed reactor, and hydrogen was thereafter supplied to the reactor at 11.0 MPa, gauge (1600 pounds per square inch, gauge), at a rate of 0.4 liters per minute for Comparative Examples 2 and 3 or 0.6 liters per minute for Comparative Example 4, together with a liquid feed comprised of 33-35% dextrose and the remainder of water. The reactor temperature was 113 degrees Celsius, with different liquid hourly space velocities being employed in each of Examples 2-4.

The process was continuously run over a period of two weeks, with product samples being drawn on a number of consecutive days within that timeframe. All amounts are reported as percent by total weight of the product mixture, with the balance of the product mixture being water.

TABLE 2

| Sample Id | LHSV | Gas flow rate L/min | glucose % | mannitol % | sorbitol % | Iditol % | maltitol % | Gluconic acid % | PG ppm | EG ppm | Glycerol ppm |
| --- | --- | --- | --- | --- | --- | --- | --- | --- | --- | --- | --- |
| Raney | 2 | 0.6 | 5.9 | 0.35 | 28.02 | 0.00 | 0.04 | 0.26 | 7.7 | 20.78 | |
| Raney | 1 | 0.4 | 1.73 | 0.64 | 31.66 | 0.00 | 0.03 | 0.13 | 12.60 | 39.73 | 71.06 |
| Raney | 0.6 | 0.4 | 0.69 | 0.58 | 34.31 | 0.05 | 0.21 | 0.06 | 10.34 | 22.78 | 48.58 |

EXAMPLE 5

A sulfided ruthenium on carbon catalyst including 2 percent of ruthenium and 1 percent of sulfur based on the total weight of the catalyst was loaded into a 30 cubic centimeter fixed bed reactor, and hydrogen was thereafter supplied to the reactor at 12.4 MPa, gauge (1800 pounds per square inch, gauge) at a rate of 0.4 liters per minute, together with a liquid feed comprised of 25% dextrose and the remainder of water. The reactor temperature was 170 degrees Celsius, and the liquid hourly space velocity was 0.7 hr$^{-1}$.

The process was continuously run over a period of two weeks, with product samples being drawn on a number of consecutive days within that timeframe. All amounts are reported as percent by total weight, with the balance being water.

TABLE 3

| Sample Id | Erythritol % | xylitol % | Arabitol % | Mannitol % | Sorbitol % | Iditol % |
|---|---|---|---|---|---|---|
| RuS/C | 0.43 | 1.26 | 2.03 | 4.21 | 10.44 | 7.29 |

EXAMPLES 6-9

A sponge nickel catalyst was loaded into a 30 cubic centimeter fixed bed reactor, and hydrogen was thereafter supplied to the reactor at 12.4 MPa, gauge (1800 pounds per square inch, gauge), at a rate of 0.4 liters per minute, together with a liquid feed comprised of dextrose, a sorbitol/dextrose mixture, fructose or mannitol and the remainder of water. The reactor temperature was 150 degrees Celsius, and the liquid hourly space velocity was 1 hr$^{-1}$.

The process was continuously run over a period of two weeks, with product samples being drawn on a number of consecutive days within that timeframe. All amounts are reported as percent by total weight, with the balance being water.

TABLE 4

| Feed | Mannitol | Sorbitol | Dulcitol | Iditol |
|---|---|---|---|---|
| 20% dextrose | 4.07 | 10.39 | 0.82 | 3.12 |
| 20% fructose | 7.76 | 9.27 | 0 | 2.00 |
| 20% dextrose/20% sorbitol | 5.86 | 28.18 | 0 | 4.99 |
| 14% mannitol | 7.20 | 4.74 | 0.61 | 1.36 |

What is claimed is:

1. A process for making isoidide, comprising:
   providing a feed including dextrose;
   providing hydrogen;
   providing a catalyst;
   contacting the dextrose-containing feed with the catalyst and with the hydrogen, and producing an iditol-enriched mixture of hexitols from the dextrose-containing feed through reaction of the feed with hydrogen in the presence of the catalyst;
   dehydrating the iditol-enriched mixture of hexitols to provide an isohexides product mixture including isoidide; and
   recovering isoidide from the isohexides product mixture.

2. The process of claim 1, wherein the catalyst is a sulfided ruthenium on carbon catalyst or a sponge nickel catalyst.

3. The process of claim 2, wherein hydrogen is provided at from 8.3 to 17.2 MPa, gauge, and the feed is reacted with the hydrogen at a temperature between 100 degrees Celsius and 200 degrees Celsius.

4. The process of claim 3, wherein hydrogen is provide at from 11.0 to 13.8 MPa, gauge, and the feed is reacted with the hydrogen at a temperature between 130 degrees Celsius and 180 degrees Celsius.

5. A process for making isoidide, comprising:
   providing a feed including dextrose;
   providing hydrogen;
   providing a catalyst;
   contacting the dextrose-containing feed with the catalyst and with the hydrogen, and producing an iditol-enriched mixture of hexitols from the dextrose-containing feed through reaction of the feed with hydrogen in the presence of the catalyst;
   recovering iditol from the iditol-enriched mixture of hexitols; and
   dehydrating the recovered iditol to produce isoidide.

6. The process of claim 5, wherein the catalyst is a sulfided ruthenium on carbon catalyst or a sponge nickel catalyst.

7. The process of claim 6, wherein hydrogen is provided at from 8.3 to 17.2 MPa, gauge, and the feed is reacted with the hydrogen at a temperature between 100 degrees Celsius and 200 degrees Celsius.

8. The process of claim 7, wherein hydrogen is provide at from 11.0 to 13.8 MPa, gauge, and the feed is reacted with the hydrogen at a temperature between 130 degrees Celsius and 180 degrees Celsius.

9. The process of claim 5, wherein sorbitol is recovered from the iditol-enriched mixture of hexitols.

10. The process of claim 9, wherein at least a portion of the recovered sorbitol is dehydrated to provide isosorbide.

11. The process of claim 10, wherein the isosorbide is directly epimerized without further purification to provide additional isoidide.

12. The process of claim 1, wherein isosorbide is recovered from the isohexides product mixture, and at least a portion of the recovered isosorbide is epimerized to produce additional isoidide.

* * * * *